United States Patent [19]

Villavicencio et al.

[11] Patent Number: 5,198,074

[45] Date of Patent: Mar. 30, 1993

[54] PROCESS TO PRODUCE A HIGH QUALITY PAPER PRODUCT AND AN ETHANOL PRODUCT FROM BAMBOO

[75] Inventors: Eduardo J. Villavicencio, Mexico City, Mexico; Jose B. Dos Santos, Recife, Brazil

[73] Assignee: Companhia Industreas Brasileiras Portela, Recife, Brazil

[21] Appl. No.: 800,414

[22] Filed: Nov. 29, 1991

[51] Int. Cl.[5] .......................... D21C 1/02; D21C 3/26
[52] U.S. Cl. ........................................ 162/15; 162/16; 162/19; 162/21; 162/22; 162/68; 162/72; 162/94; 127/37; 435/99; 435/163; 435/165
[58] Field of Search ...................... 162/94, 72, 68, 16, 162/15, 19, 24, 21, 22; 127/37; 435/99, 163, 165

[56] References Cited

U.S. PATENT DOCUMENTS

| | | | |
|---|---|---|---|
| 1,323,540 | 12/1919 | Moore . | |
| 2,893,919 | 7/1959 | Friedrichshafen-Windhag | 195/39 |
| 3,238,088 | 3/1966 | Villavicencio et al. | 162/19 |
| 3,479,248 | 11/1969 | Nobile | 162/16 |
| 3,537,142 | 11/1970 | Villaviencio | 19/26 |
| 3,877,110 | 4/1975 | McCloskey et al. | 19/66 |
| 4,070,232 | 1/1978 | Funk | 162/16 |
| 4,347,101 | 8/1982 | Villavicencio | 162/19 |
| 4,368,268 | 1/1983 | Gong | 435/163 |
| 4,517,298 | 5/1985 | Tedder | 435/160 |
| 4,529,699 | 7/1985 | Gerez et al. | 435/160 |
| 4,564,595 | 1/1986 | Neves | 435/163 |
| 4,612,286 | 9/1986 | Sherman | 435/157 |
| 4,635,322 | 1/1987 | Villavicencio et al. | 19/66 |
| 4,681,935 | 7/1987 | Forss | 536/56 |
| 4,689,117 | 8/1987 | Villavicencio | 162/19 |
| 4,699,691 | 10/1987 | Villavicencio | 162/19 |
| 4,708,746 | 11/1987 | Hinger | 162/68 |
| 4,840,903 | 6/1989 | Wu | 435/165 |
| 4,857,145 | 8/1989 | Villavicencio | 162/19 |
| 4,889,591 | 12/1989 | Villavicencio | 162/20 |
| 4,952,504 | 8/1990 | Pavilon | 435/163 |

Primary Examiner—Steve Alvo
Attorney, Agent, or Firm—Michael J. McGreal

[57] ABSTRACT

A method of producing high quantities of ethanol and a high quality pulp to produce a variety of papers. The method comprises preparing the bamboo by chipping, shredding and washing. This bamboo fiber is then processed in two stages of prehydrolysis to separate the ethanol producing portion from the pulp producing portion. The ethanol producing portion is condensed and subject to enzymatic hydrolysis and fermentation to produce an ethanol product. The pulp producing portion is processed in two stages of digestion to produce a pulp in high yield that is suitable to produce a variety of papers.

16 Claims, 1 Drawing Sheet

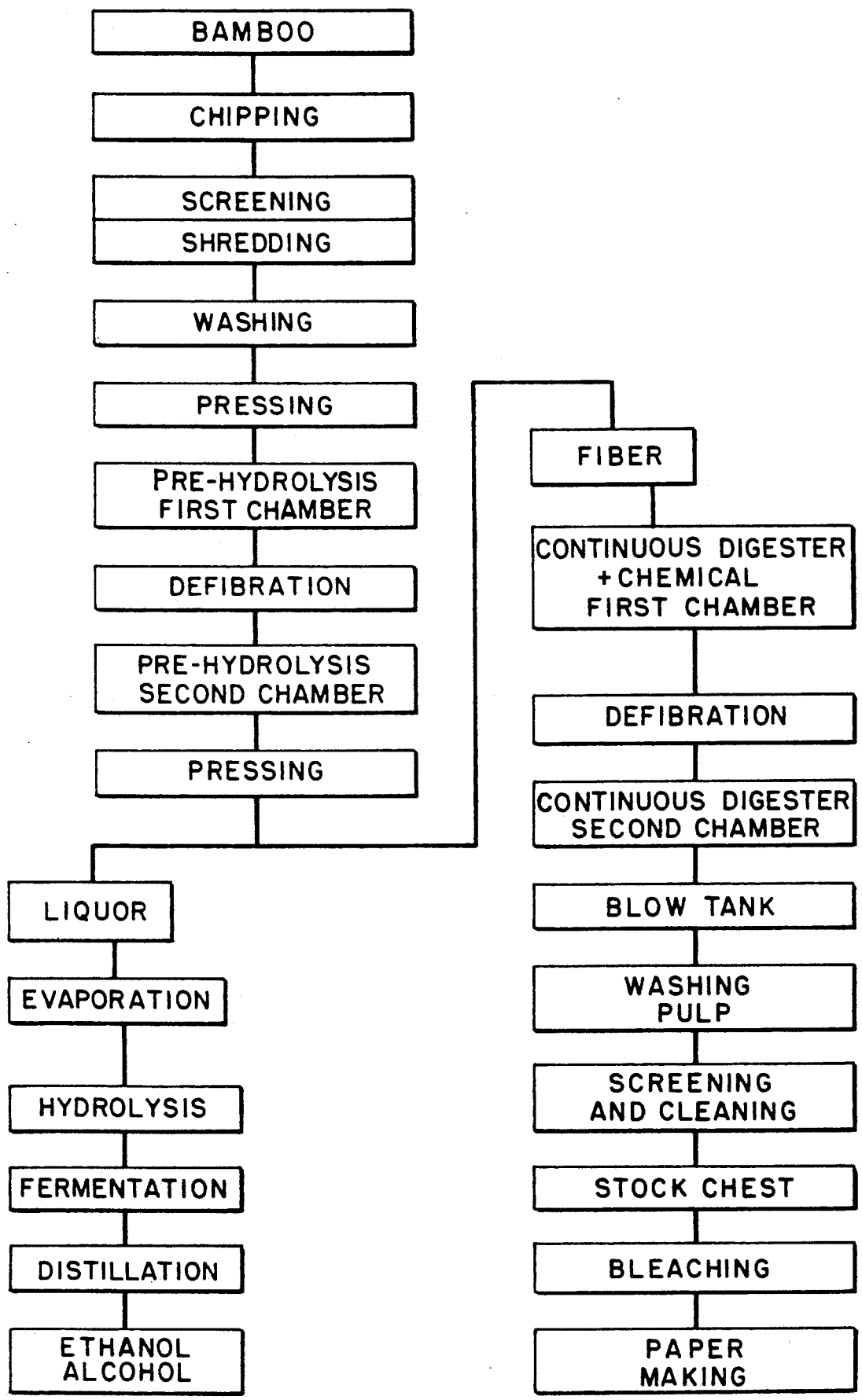

PROCESS TO PRODUCE A HIGH QUALITY PAPER PRODUCT AND AN ETHANOL PRODUCT FROM BAMBOO

This invention relates to a process for converting bamboo into a fiber source suitable for producing a high quality paper and to produce an ethanol product in relatively high volumes.

Bamboo has been used as a fiber source for making paper products. Bamboo has also been used as a source of substances that can be converted to ethanol by fermentation. Various cellulosic and starch sources are known to be useful to produce ethanol by means of fermentation. However, there has been no process for processing bamboo which could be economically competitive with other sources of fiber for producing a pulp for making high quality paper or with other sources of sugar or starch for producing sufficient quantities of fuel grade ethanol. As a result, bamboo has not been looked upon as a valuable resource material. This is the case since prior processes did not have the dual objective of making a pulp suitable to make newsprint and high quality papers and at the same time to produce a comparatively high volume of fuel grade ethanol. By producing two products that are in demand, the economics of bamboo as an industrial raw material is changed. With two products to sell the processing of bamboo becomes cost effective. There is less wastage. More of the bamboo is used to produce products. There is likewise less pollution with more raw material becoming saleable product. In addition, bamboo is a renewable resource. It is a plant that grows rapidly with a high annual yield per hectare.

Bamboo is present in the world in many varieties. One prevalent variety, and one which contains relatively long fibers is *Bambusa vulgaris*. This will contain about 49 percent cellulose, 15 percent lignin, 0.5 percent galactose, 1.2 percent arabinose and 10.9 percent xylose. The remainder will be primarily pith and silica. From this assay the cellulose would be converted to a pulp for papermaking and starches, to ethanol through fermentation.

In U.S. Pat. No. 4,857,145 there is disclosed a process for producing a usable paper pulp from bamboo. This process consists of shredding the bamboo when in the form of a stalk fragment, washing the shredded bamboo and wet depithing the shredded and washed bamboo. The fiber then undergoes two stages of digestion in tubular digesters, with a rapid pressure drop between stages. In the first stage, black liquor is added as the digestion chemical. In the second stage, a caustic solution is the digestion chemical. However, a prime part of the processing in this patent resides in the bamboo preparation steps. These bamboo preparation steps are not used in the present processing of bamboo. A different processing is needed in order to produce a quality pulp and large volumes of ethanol from bamboo.

The technique of digesting a fiber in a tubular digester is also shown in U.S. Pat. No. 3,238,088; U.S. Pat. No. 4,699,691; and U.S. Pat. No. 4,689,117. These patents disclose different multi-stage techniques for processing a fiber source where there is a pressure drop between stages. There is also disclosed the use of a refiner between stages. The basic technique is set out in U.S. Pat. No. 3,238,088 with particular modifications and improvements set out in U.S. Pat. No. 4,689,117 and U.S. Pat. No. 4,699,691. In U.S. Pat. No. 4,689,117 bleach is added as a digestion chemical and is added to the pulp going to a second state digestion just prior to depressurization. In U.S. Pat. No. 4,699,691 a similar process is utilized but with a second addition of digestion chemicals added just prior to reduction of pressure on the pulp and the flow of pulp to the second digester. These are both useful techniques for processing non-wood fibers such as bagasse to a pulp for papermaking. However, there is not disclosed the use of bamboo or a technique for also producing ethanol while producing a pulp that can be used to produce high quality papers.

In U.S. Pat. No. 2,893,919 there is disclosed a process for recovering carbohydrate values from a papermaking waste stream and converting these carbohydrate values to ethanol through fermentation. Hemicellulose will be one source for these carbohydrate values. Related processes for concurrently making paper products and ethanol are disclosed in U.S. Pat. No. 3,479,248 and U.S. Pat. No. 4,681,935. The starting material is a wood and the source of the ethanol is from the fermentation of the hemicellulose content of the liquid stream from pulp processing. Also as fuels have gotten more costly, processes have been developed to convert biomasses to ethanol. Illustrative of such processes are those disclosed in U.S. Pat. No. 4,612,286 and U.S. Pat. No. 4,952,504. These patents give a detailed description of processes for the conversion of biomass to ethanol. However, none of these references discloses a process for making ethanol in high volumes along with a high quality pulp from bamboo. This is a unique raw material source. Interestingly, through the use of the present newly developed processes, large volumes of ethanol and a high quality pulp for papermaking can be produced concurrently.

BRIEF DESCRIPTION OF THE INVENTION

These various problems of the prior art are solved by the use of the processes set out in this application for patent. Bamboo is harvested and stacked. It has a relatively long storage life, much longer than bagasse. Bamboo can be stored for 6 months or more with little degradation. The bamboo stalks are then chipped and the chips screened to separate out a fraction for further processing. The bamboo chips can also be stored. The bamboo chips are then shredded, washed and pressed to remove most of the wash water. The chipped and shredded bamboo then undergoes two stages of prehydrolysis. The first stage is preferably at a higher temperature and pressure than the second stage. The prehydrolysis is conducted using steam, preferably at a pressure of about 7.5 to 12 kg/cm$^2$ in the first stage with the pressure in the second prehydrolysis stage being at least about 0.5 to 3 kg/cm$^2$ less than the pressure in the first stage, and preferably at least about 1.0 to 2 kg/cm$^2$. There is a rapid pressure drop from the first stage to the second stage of prehydrolysis. The residence time of the fiber in the first stage is about 5 to 60 minutes, and in the second stage about 10 to 90 minutes. After the second stage of prehydrolysis the pressure on the fiber is reduced to ambient in a blow tank. The prehydrolysis is conducted on a continuous basis in tubular digesters.

The defibration that is effected during prehydrolysis can be enhanced by the depressurization between prehydrolysis being conducted by passing through a defibrator. The abrasion of the plates in a defibrator serves to assist in the opening of the fiber bundles.

After the blow tank, the fiber slurry is flowed to an extractor press in order to separate the fibers from the liquid stream. The fiber portion in the form of a pulp is sent to digesters for papermaking and the liquid stream rich in sugars and starch is sent to fermentation. A concurrent step consists of the removal of furfural from the steam portion of the liquids from the blow tank. This is accomplished by condensing the steam and stripping the furfural. The liquid fraction from the extractor press is passed to fermentation for the conversion of sugars and starch to ethanol.

The fiber portion is then processed by continuous digestion in a two or three stage digestion process. The processing consists of contacting the fiber with steam and digestion chemicals, which can be black liquor from the process, in a first stage continuous tubular digester for a period of time of about 5 to 60 minutes and preferably about 10 to 30 minutes. The pressure will be about 7 to 12 kg/cm$^2$, and preferably about 8 to 10 kg/cm$^2$. At the completion of the first stage of digestion the pressure on the fiber is rapidly decreased at least about 0.5 to 3 kg/cm$^2$, and preferably at least about 1 to 2 kg/cm$^2$. Digestion is then repeated in a second continuous tubular digester at a first lower pressure, but with the addition of digestion chemicals. The retention time in the second stage tubular digester is about 20 to 90 minutes and preferably about 45 to 75 minutes. At the exit of the second tubular digester the pressure on the fiber is rapidly reduced at least about 0.5 to 3 kg/cm$^2$, and preferably at least about 1 to 2 kg/cm$^2$. At this point, the fiber can be flowed to a third digester or pass to a blow tank. If flowed to a third digester the fibers will be processed in this third digester in a manner similar to that of the first and second digester but at a yet lower pressure. After the optional third stage of digestion it will then flow to the blow tank. In the blow tank, the pressure on the fibers is dropped to atmospheric pressure. The pulp is then processed for feeding to a paper machine. This includes pulp washing, pulp screening and cleaning and pulp bleaching. The type of bleaching that would be used would depend on the product to be produced.

In the processing of the liquid stream, this stream is condensed to a starch and glucose concentration of about 10 to 20 percent by weight. An alpha amylase is added to convert the starch to glucose in a first stage of fermentation and an enzyme then added to convert the glucose to ethanol in a second stage of fermentation.

The yield of pulp per metric ton of input bamboo fiber will be about 50 to 60 percent depending on the degree of bleaching. The yield of ethanol after fermentation will be at least about 80 liters of 93.8 percent ethanol per ton of bamboo fiber.

BRIEF DESCRIPTION OF THE DRAWING

The FIGURE is a block diagram of the process for producing a pulp for papermaking and an ethanol product.

DETAILED DESCRIPTION OF THE INVENTION

The objective of the present process is to produce two economically useful products. One product is a pulp that can be used for making a quality paper. The other product is ethanol which can be used as a fuel or as a reactant to produce other chemicals. By producing two economically useful products, the process is economically viable.

In the present process, the bamboo is first chipped to bamboo fragments of a size of about 4 cm to 8 cm. thick and preferably to about 6 cm. The other dimensions will be that of the bamboo stalk. A series of knives in a chipper converts the bamboo stalks to chips. The bamboo chips are then screened to provide a chip fraction where the chips are no smaller than about 0.4 cm. Oversized chips are also removed. The screened chip fraction is then shredded to open the chips to masses of partially deaggregated fibrous bundles. These fibrous bundles are then washed to remove silica and other solids, pith, some lignin and solubles. Washing is conducted with water, optionally containing alpha amylase which aids in removing starch values. After washing the fibrous bundles are pressed to remove water and to establish a consistency of about 20% to 50%, and preferably a consistency of about 40%. The wash water is reused for fiber washing, and at a subsequent time can be treated for its starch and sugar content by flow to an evaporator.

Fiber washers that can be used effectively are those set out in U.S. Pat. No. 3,877,110 and U.S. Pat. No. 4,635,322. These patents disclose a U-shaped washer where the fiber bundles are successively immersed and reimmersed in the washing liquor, which will be water. The fiber bundles are fed to the washer by means of a pin feeder. The fiber bundles enter one leg of the U shaped washer and exit the other leg. At the loop of the U various solid materials settle and are removed. The washer delivers the washed fiber to a conveyor for transport to a press. The water released from the fiber during pressing is recycled to the washer.

The consistency of the fiber entering the washer is about 40% to 60% and preferably about 50% with the consistency of the fiber leaving the washer is about 20% to 50%, and preferably about 40%. Make-up water is continuously added to the wash water as is alpha amylase. The fiber entering the first stage of prehydrolysis has a consistency of about 20% to 50%, and preferably about 40% and an adjusted pH of greater than about 6 and preferably about 7.

The fiber bundles now at the desired water content are conveyed to the input screw feeder to a continuous digester to a first stage of prehydrolysis. A digester as described in U.S. Pat. No. 3,238,088 is preferred. The fiber is fed to the first stage of prehydrolysis in a continuous tubular digester at the consistency that it exits the screw feeder of preferably about 40%. Steam is added at a pressure of about 7.5 kg/cm$^2$ to 12 kg/cm$^2$, and preferably about 9 kg/cm$^2$. A weak black liquor at an acidic pH can also be added. The retention time in the first stage is at least about 5 minutes to 60 minutes and preferably about 20 minutes to 40 minutes, and most preferably about 30 minutes. The fiber is then discharged from the first prehydrolysis tubular chamber and undergoes a rapid pressure reduction. The pressure is rapidly reduced at least about 0.5 to 3 kg/cm$^2$ and preferably at least about 1.0 to 2.0 kg/cm$^2$. In a preferred embodiment, the fibers are flowed to a refiner to a step of concurrent defibration and rapid pressure reduction. The plate spacing in the defibrator is about 0.01 mm to 5 mm.

The fiber then passes to the second stage of prehydrolysis in a second tubular digester. The pressure in this prehydrolysis digester will be from about 7 kg/cm$^2$ to 11.5 kg/cm$^2$, and preferably about 7.5 to 9 kg/cm$^2$. The water content of the fiber in the second prehydrolysis stage is about the same for the first stage of prehydrolysis. The retention time in the second prehydrolysis tubular chamber is from about 10 minutes to 90 minutes, preferably about 30 to 75 minutes and most preferably about 60 minutes. The ratio of the time of the fiber in the second stage of prehydrolysis to the first stage is about 2:1. The fiber from the second prehydrolysis stage flows to blowdown at atmospheric pressure in a blow tank. The fiber slurry is then recovered and sent to a press which separates the prehydrolysis liquor from the fiber. The prehydrolysis liquor is sent to fermentation processing to produce ethanol while the fiber is sent to digestion to produce a papermaking pulp. The blowdown steam is flowed to a heat exchanger where the steam is condensed. The condensed steam is then sent to a stripper column where furfural is recovered. The amount of furfural recovered will range from about 1 to 3 percent by weight of the bamboo processed.

At this point in the processing, there is a split into two different fractions. One fraction is the liquid fraction from prehydrolysis which optionally can contain some water from the washing step. The liquid fraction from prehydrolysis has a Ph of about 6.5 to 7. This fraction is evaporated using excess process heat. The evaporator operates above about 75° C., and preferably above about 90° C. and at a vacuum. The starch and glucose concentration after evaporation is about 10 percent to about 20 percent by weight and preferably about 15 percent by weight. This is cooled to less than about 70° C. and an alpha amylase enzyme is added to hydrolyze the starch to glucose. This solution is then cooled to less than about 60° C., and preferably to less than about 40° C. and an enzyme added to convert the glucose to ethanol. A suitable enzyme is provided by the saccharomose servisae yeast. After fermentation the fermentate is subject to distillation to produce a product that is about 93.8 percent ethanol, the remainder being primarily water. This can be increased to about 100 percent through the use of azeotropic distillation. The yield of ethanol will be in excess of about 80 liters of 93.8 percent ethanol per ton of bamboo processed, and preferably at least about 100 liters per ton. This ethanol product is then passed to storage.

Concurrent with the processing of the liquid fraction the fiber fraction is being processed. The fiber is continuously fed to the first stage pulp tubular digester along with steam and black liquor from the subsequent post digestion wash step. The steam pressure in the first tubular digestion chamber is about 7 kg/cm$^2$ to 12 kg/cm$^2$, and preferably about 9 kg/cm$^2$. The tubular digester is preferably of the type described in U.S. Pat. No. 3,238,088. The retention time in the first tubular digestion chamber is about 5 minutes to 60 minutes, and preferably about 10 to 30 minutes. The ratio of water on fiber is about 2:1 to about 5:1 and preferably about 3:1. The main components of the black liquor are sodium hydroxide and sodium carbonate. The black liquor will have a Ph of about 10.5 to about 13.

The fiber then flows from the first tubular digester to the second tubular digester. As the fiber flows from the first tubular digester to the second tubular digester, it undergoes a rapid pressure drop of at least about 0.5 to 3 kg/cm$^2$, preferably at least about 1.5 to 2 kg/cm$^2$. As a particularly useful embodiment, the fiber is preferably defibrated in a refiner and the pressure concurrently rapidly reduced. In the refiner the plates are spaced at about 0.01 to 5 mm. The fiber gets defibrated in the defibrator as a result of the concurrent rapid pressure reduction and mechanical action and flows into a second tubular digester for a second stage of digestion. The pressure in the second tubular digester is that of the first tubular digester, less the pressure drop. The digestion chemicals are preferably added to the fibers prior to the pressure drop. This assists in the penetration of the chemicals into the fibers. The digestion chemicals consist of a caustic solution which contains about 16 to 20 weight percent by weight sodium hydroxide, and preferably about 18 weight percent sodium hydroxide. The digestion chemicals are added to give a water to fiber ratio of about 3 to 1 to about 10 to 1, and preferably about 5 to 1 to 8 1. The sodium hydroxide that is not consumed in the second tubular digester will be a part of the black liquor that is used as the digestion chemical in the first stage of digestion. The retention time in the second tubular digester is from about 20 to 90 minutes, and preferably about 45 to 75 minutes. After the second stage of digestion, the fiber is preferably flowed to a blow tank where the pressure is reduced to atmospheric pressure. In the alternative the fiber can be flowed to a third tubular digester. In such a case the pressure would be rapidly dropped at least about 0.5 to 3 kg/cm$^2$ and preferably at least about 1.5 to 2 kg/cm$^2$. In addition, further digestion chemicals can be added and the fiber can be refined before entering the third tubular digester in the same manner as prior to entering the second digester.

After reaching atmospheric pressure in the blow tank the fiber is flowed to washing. The washing is usually a single stage of countercurrent washing using fresh water or paper mill water. This consists of flowing the water countercurrent to the pulp in two or three stages. In this way the cleanest fiber is contacted with the freshest water. Washing is continued until the total alkalinity of the fiber is reduced to less than about 6 kg per ton of pulp.

In the next step the fiber is screened and cleaned by centrifuging. The screening removes the large fiber bundles that have not been opened. These are recycled to the first tubular digestion chamber. The centrifuging removes excess liquid. This wash liquid makes up the black liquor that is used as the first stage digestion liquid. This fiber is then forwarded to a bleaching sequence depending on the paper that is to be produced. If a kraft-like paper, a high K-number paper is to be produced, then the bleaching step can be deleted. Depending on the paper product to be produced, different bleaching sequences will have to be used. The pulp from this process can be used to produce a wide range of paper products.

The production of pulp from the bamboo stalk is in the range of about 0.5 to 0.6 metric tons of pulped fiber per metric ton of bamboo, both on a bone dry basis. This in combination with the at least 80 liters of ethanol makes bamboo an economically useful source for both fuel grade ethanol and pulp for papermaking.

The processes disclosed in this specification may be changed as to one or more steps. However, any processes which incorporate such steps would be uncompassed by the present invention.

EXAMPLE

Bamboo stalks are chipped to a size of about 6 cm in thickness. The other dimensions of the chips are the dimensions of the bamboo stalk. The chips are screened to remove larger bamboo pieces and the chips sent to a shredder. The shredder processes 35,000 kilograms (kgs) of bamboo per hour. The shredding opens the chips into fiber bundles. The fiber bundles are fed directly to a PEADCO washer after being shredded. The fiber bundles enter the washer through a pin feeder at a moisture content of about 30% by weight and exit at a moisture content of more than 80% by weight. The washer also contains the enzyme alpha amylase which serves to release starches from the bamboo. The washed fiber bundles go to pressing which reduces the moisture content to about 80% by weight.

This washed fiber is conveyed to a first stage of prehydrolysis. The fiber is fed to a tubular digester which has an internal diameter of 1.37 meters and a length of 10.9 meters. The fiber is fed at the rate of 24,255 kgs per B.D. (bone dry basis) hour. Weak black liquor is added to produce a water on fiber of 3 to 1. The weak black liquor has a pH of 4.5. The weak black liquor consists of primarily dissolved sugars and lactic acid. Steam is added to this tubular digester to a pressure of 9 kgs/sq.cm. The retention time of the fiber in this digester is 30 minutes. The fiber exits the first prehydrolysis digester and flows to a disc refiner which refines the fiber and simultaneously rapidly drops the pressure 1.8 kgs/sq.cm. The fiber is then fed to a second tubular prehydrolysis digester having the same dimensions as the first digester. The pressure in the second digester is 7.5 kgs/sq.cm. and the retention time is 60 minutes. The fiber exits the digester and goes to a blow tank where the pressure on the fiber is reduced to atmospheric.

At this point the steam from the blow tank is sent to condensation and stripping. Furfural is stripped from the steam and recovered. The wet fibers are sent to a press to reduce the moisture content to 60% by weight. The removed water is sent to conversion to ethanol. The fibers are sent to digestion to a pulp for making paper products.

The liquid fraction is evaporated at 90° C. under vacuum to a starch/sugar content of about 15% by weight. This concentrated liquor is cooled to 20° C. and alpha amylase added to hydrolyze fermentation to ethanol. Saccharomose servisae is then added to the liquor to convert the simple sugars to ethanol. This liquor is then distilled to produce an ethanol product of 93.8% ethanol. This is 150 liters of ethanol per metric ton of bamboo processed.

The fiber fraction is simultaneously fed to a continuous digester and black liquor added. The black liquor has a pH of 11 and is comprised primarily of caustic soda and sodium carbonate. The black liquor is added to produce a water on fiber of 3 to 1. Steam is added to this digester to increase the pressure to 9 kgs/sq.cm. The retention time in this digester is 15 minutes. The fiber exits this digester and is flowed to a disc refiner. In the refiner the fiber is mechanically worked and the pressure on the fiber is rapidly reduced 1.5 kgs/sq.cm. Prior to entering the refining chamber a digestion liquor consisting of 18% NaOH by weight is added to bring the water on fiber content to 5 to 1. The fiber flows to a second digester for a retention time of 60 minutes. The pressure in this digester is 7.5 kgs/sq.cm. The fiber exits this digester and flows to a blow tank. The blow tank reduces the pressure to atmospheric. Black liquor is recycled to the first digester. The fiber is washed in a three stage countercurrent washer with fresh water until the caustic content is reduced to less than 0.2% by weight. This fiber is screened and cleaned and the acceptable fiber sent to the stock chest. From the stock chest it will be sent to bleaching or directly to papermaking depending on the paper product to be made. The fiber in the stock chest is 60% of the bamboo processed.

What we claim is:

1. A process for producing ethanol and a high quality pulp for papermaking comprising:
   (a) deaggregating bamboo pieces into a fibrous mass by shredding;
   (b) washing the deaggregated fibrous mass with water containing enzymes suitable to assist with sugar and starch solubilization;
   (c) removing wash water from the washed fibrous mass and flowing and retaining the remainder of the wash water for fiber washings;
   (d) conveying the fibrous mass at a pH of greater than about 6 to a first stage of continuous prehydrolysis with steam at a pressure of about 7.5 to 12 kg/cm$^2$ for a first period of time;
   (e) discharging said fibrous mass from the first stage of prehydrolysis and rapidly decreasing the pressure on said fiber at least about 0.5 to 3 kg/cm$^2$;
   (f) flowing said fiber mass into a second stage of continuous prehydrolysis at a pressure greater than about 7 kg/cm$^2$ for a second and longer period of time;
   (g) decreasing the pressure on a prehydrolized fiber to atmospheric pressure and recovering (i) a liquid stream which contains substances for the production of ethanol, (ii) a fiber for papermaking and (iii) steam containing furfural;
   (h) processing said liquid stream by concentrating the substances for the production of ethanol and by contact with enzymes capable of converting such substances to ethanol, thereby converting substantial amounts of such substances to ethanol;
   (i) processing said fiber for papermaking by means of at least two stages of chemical digestion with a step of rapidly reducing the pressure between steps of digestion to produce a paper pulp; and
   (j) recovering a useful ethanol product and a pulped fiber useful in papermaking.

2. A process as in claim 1 wherein the bamboo is deaggregated by converting said bamboo into chips and shredding said chips.

3. A process as in claim 1 wherein the enzyme added to said wash water is an alpha amylase.

4. A process as in claim 1 wherein the ratio of the time of said fiber in said second stage of continuous prehydrolysis to the time of said fiber in said first stage of continuous prehydrolysis is at least about 2:1.

5. A process as in claim 4 wherein the time of the fiber in said first stage of continuous prehydrolysis is about 5 minutes to 60 minutes and in said second stage of continuous prehydrolysis of about 10 to 90 minutes.

6. A process as in claim 1 wherein from said first stage of continuous prehydrolysis to said second stage of continuous prehydrolysis the pressure on said fiber is rapidly decreased about 1 to 2 kg/cm$^2$.

7. A process as in claim 1 wherein said furfural is in the steam after the pressure on the prehydrolyzed fiber is reduced to atmospheric pressure and said furfural is recovered from said steam.

8. A process as in claim 1 wherein said fiber for papermaking is contacted in a first stage of chemical digestion with recycled digestion liquor at a pressure of about 7 to 12 kg/cm$^2$ for a first period of time.

9. A process as in claim 8 wherein after said first stage of chemical digestion the pressure on said fiber is rapidly reduced at least about 0.5 to 3 kg/cm$^2$.

10. A process as in claim 9 wherein after the first stage of chemical digestion and concurrent with the pressure on said fiber being rapidly reduced, said fiber is defibrated.

11. A process as in claim 9 wherein prior to the reduction of pressure on said fiber after the first stage of chemical digestion, digestion chemicals comprising sodium hydroxide having a sodium hydroxide content of about 16 to 20 percent by weight are added to produce a water to fiber ratio of about 3:1 to 10:1.

12. A process as in claim 11 wherein after said addition of digestion chemicals and rapid reduction of pressure said fiber is digested for a second period time in a second stage of chemical digestion.

13. A process as in claim 12 wherein said fiber is digested in said first stage of chemical digestion for a period of about 5 to 60 minutes and in said second stage of chemical digestion for a period of about 20 to 90 minutes.

14. A process as in claim 1 wherein said liquid stream is evaporated to produce a liquid stream of about 10 to 20 percent glucose or glucose yielding substances, treated with alpha amylase to convert complex carbohydrates to glucose, and contacted with an enzyme to convert the glucose to ethanol.

15. A process as in claim 10 wherein the enzyme to convert starches to glucose is saccharomose yeast.

16. A process as in claim 1 wherein the steam containing furfural is condensed and the furfural recovered.

* * * * *